United States Patent [19]

Nakai et al.

[11] Patent Number: 4,731,209

[45] Date of Patent: Mar. 15, 1988

[54] METHOD OF MAKING STANDARD COLOR MODELS USED FOR JUDGING BEEF

[75] Inventors: Hiroyasu Nakai, Matsudo; Toshio Ikeda, Ibaragi; Shiro Ando, Ibaragi; Kyohei Ozutsumi, Ibaragi, all of Japan

[73] Assignee: National Institute of Animal Industry, Ibaragi, Japan

[21] Appl. No.: 843,311

[22] Filed: Mar. 24, 1986

[30] Foreign Application Priority Data

Apr. 30, 1985 [JP] Japan ............................ 60-93298

[51] Int. Cl.⁴ .................. B29C 39/44; G01J 3/46
[52] U.S. Cl. ........................ 264/40.1; 264/299; 356/243; 356/421
[58] Field of Search ............... 356/421, 422, 243, 402; 264/222, 40.1, 78, 225, 219, 220, 223, 226, 245, 299; 428/15, 16

[56] References Cited

U.S. PATENT DOCUMENTS

| | | | |
|---|---|---|---|
| 3,190,947 | 6/1965 | Norcross | 264/166 |
| 3,707,726 | 12/1972 | Stearns | 356/402 |
| 3,781,909 | 12/1973 | Stearns | 356/402 |
| 3,799,668 | 3/1974 | McVeigh | 356/243 |
| 3,949,502 | 4/1976 | Carr | 428/15 |
| 4,364,880 | 12/1982 | Howse | 264/299 |
| 4,523,852 | 6/1985 | Bauer | 356/243 |
| 4,559,189 | 12/1985 | Wegener, II | 264/39 |
| 4,668,457 | 5/1987 | Nakai et al. | 264/227 |

FOREIGN PATENT DOCUMENTS 2541451 8/1984 France .

OTHER PUBLICATIONS

Paint Testing Manual, by Gardner R. Sward, 12th edition, 1961, pp. 10-12, 21-22, 25-26.

*Primary Examiner*—Jan H. Silbaugh
*Assistant Examiner*—J. F. Durkin, II
*Attorney, Agent, or Firm*—Martin A. Farber

[57] ABSTRACT

Colors of sections of several beef carcasses are measured and the colors are classified into a predetermined number of grades of tone. Colored silicon plastic sol is poured in a glass cell for each grade, and the color of each plastic sol is matched with the classified beef color. The plastic sol is poured into a female mold having an irregular surface resembling a surface of a section of a beef, and the plastic is taken out from the female mold when it becomes gel.

6 Claims, 2 Drawing Figures

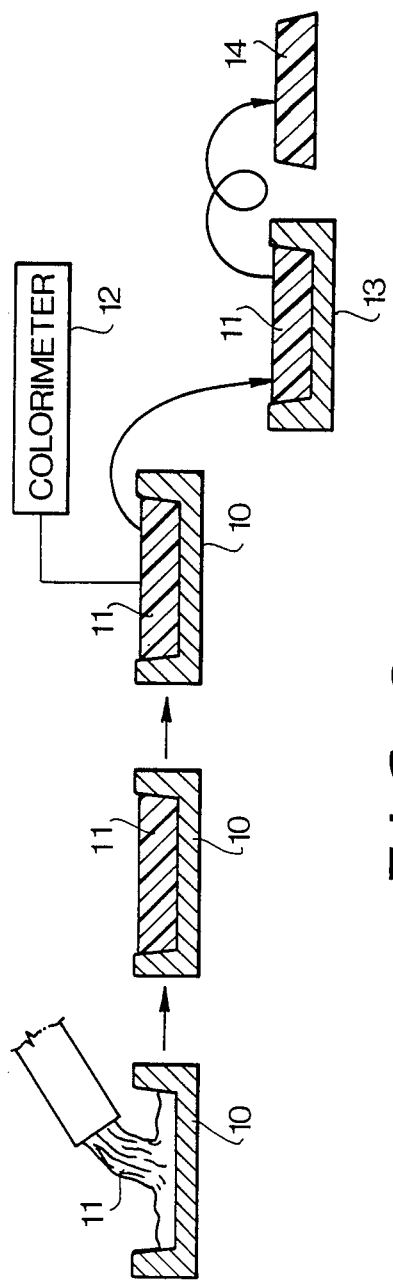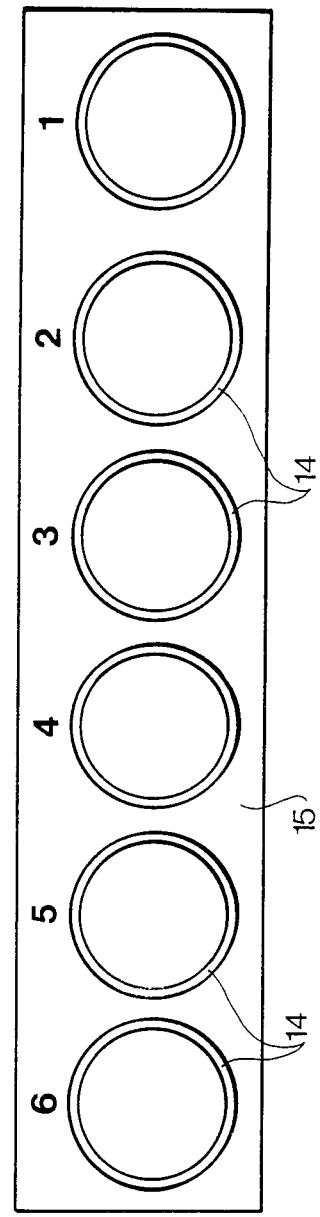

METHOD OF MAKING STANDARD COLOR MODELS USED FOR JUDGING BEEF

BACKGROUND OF THE INVENTION

The present invention relates to a method for producing a standard color model used for judging the shade and tone of beef-color.

Up to the present, the market standard of beef carcass is chiefly based on its quantity, because a simple and exact method for judging its quality has not yet been established. Accordingly, the grading of market beef carcass depends on a subjective decision of a judge. Therefore, it is necessary to provide a simple, accurate and exact method for judging the quality of meat by colorimetrically comparing the tone thereof.

The tone of beef is an important factor for determining its quality. Means for judging the quality of chemical analysis or by using a color comparator or only with human eyes are already known. However, these means involve either complex operations or expensive measuring tools. Additionally judgements were often arbitrary.

SUMMARY OF THE INVENTION

The object of the present invention is to provide a method of producing a standard color model of beef by which the shade and tone of beef can be easily, accurately and objectively compared.

According to the present invention, there is provided a method comprising measuring colors of sections of a plurality of beef carcasses by a colorimeter, classifying the colors into a predetermined number of grades of tone, pouring a colored silicon plastic sol in a glass cell for each grade, matching the color of each plastic sol with the classified beef color, pouring the plastic sol into a female mold having an irregular surface resembling a surface of a section of a beef, and taking out the plastic from the female mold when it becomes gel.

The other objects and features of this invention will become understood from the following description with reference to the accompanying drawings.

BRIEF DESCRIPTION OF THE PREFERRED EMBODIMENT

FIG. 1 is a schematic diagram showing a method according to the present invention; and FIG. 2 is a plan view of a set of standard color models of beef produced by the method of the present invention.

DETAILED DESCRIPTION OF THE PREFERRED EMBODIMENT

In order to obtain standard colorimetric values of beef for the production of color models, colors of sections of various beef carcass were measured with a colorimeter after full blooming (encrimsoning) and analyzed according to Hunter's color difference formula. The tone of each section is designated by Hunter's color values L, a, b, respectively. In an example of the present invention, six grades of tone according to the L, and b values are provided.

FIG. 2 shows the set of standard color models of the present invention comprising six color models, in which the palest one is marked with numeral 1, the darkest with numeral 6.

Referring to FIG. 1, a colored plastic sol 11 is poured into a circular glass cell 10. The color of the plastic sol 11 is measured with a colorimeter 11 and color matching was performed so as to reach the same L, a, b values as one of the six grades of tone.

The colored plastic sol 11 is then poured into a female mold 13 made of silicon plastic. The female mold 13 is provided at the bottom with an irregular surface resembling a surface of a section of a beef carcass. When the sol becomes gel, it is taken out of the female mold 13. Thus, a standard color model 14 is formed.

Since the plastic is colored and color matched by adding pigments when the plastic is still in a sol state, it is necessary to use a plastic which does not change in color when it becomes gel. Silicon resin is preferably used as such a plastic having suitable properties. The colorant must be such that it is easily dissolved in the plastic and does not fade. Pigments such as quinacridone, chromophtale, isoinrinone and titanium pigment have high light resistance and therefore, appropriate.

In accordance with the above-described method, six standard color models 14, each having different tone, were produced. As shown in FIG. 2, the models 14 are placed in a row from 1 to 6 in a transparent container 15 made of synthetic resin so as to make it possible to compare actual beef with each model.

By comparing the tone of beef with the standard color models 14 at a carcass market, the quality of beef is graded into one of the thirteen levels graduated by 0.5 points from 0.5 to 6.5. Since the judgement is based only on a comparison of the color of the meat with the standard color models, anyone can easily, accurately and quickly judge the quality of beef.

From the foregoing, it will be understood that the present invention provides a simple method for producing a set of standard color models for grading beef, wherein the color does not deteriorate in sunlight and also is highly durable.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. A method of making several standard color models graded in tone for judging beef, which comprises the steps of:
    measuring colors of sections of a plurality of beef carcasses by a colorimeter;
    classifying the colors into a predetermined number of grades of tone;
    pouring a colored plastic sol in a glass cell for each grade;
    measuring each colored plastic sol with a colorimeter and performing color matching with each colored plastic sol to reach the classififed grades of tone;
    pouring each color matched colored plastic sol into a female mold having an irregular surface resembling a surface of a section of beef; and
    taking out each colored matched colored plastic sol from the female mold when it becomes gel.

2. The method according to claim 1 wherein the plastic is silicon plastic.

3. The method according to claim 1 wherein the irregular surface is formed on the bottom of the female mold.

4. The method according to claim 1, wherein
    the step of measuring is performed after encrimsoning.

5. The method according to claim 1, wherein the step of classifying is performed by analyzing accordng to Hunter's color difference formula, with the tone of each of the sections of the beef carcasses being designated by Hunter's color values L, a, b.

6. A method for judging beef, comprising the steps of
measuring colors of sections of a plurality of beef carcasses by a colorimeter;
classifying the colors into a predetermined number of grades of shade and tone;
pouring a colored plastic sol in a cell for each grade;
measuring each colored plastic sol with a colorimeter and performing color matching with each colored plastic sol to reach the classified grades of tone;
pouring each color matched colored plastic sol into a female mold having an irregular surface resembling a surface of a section of beef;
removing each color matched colored plastic sol from the female mold when it becomes gel to obtain color models;
placing the color models in a transparent container arranged in order of palest to darkest; and
comparing the shade and tone of beef at a market with the color models, the comparison determining graduations corresponding to the color models and respectively substantially halfway between the color models.

* * * * *